United States Patent
Niemeyer et al.

[11] Patent Number: 5,400,802
[45] Date of Patent: Mar. 28, 1995

[54] EMERGENCY HEAD IMMOBILIZERS

[76] Inventors: Joan E. Niemeyer; Robert H. Schott, both of 5715 Greenton Way, St. Louis, Mo. 63128

[21] Appl. No.: 197,950

[22] Filed: Feb. 17, 1994

[51] Int. Cl.⁶ .................. A61F 5/37; A47C 20/02; A61B 19/00
[52] U.S. Cl. .................. 128/869; 128/870; 5/637
[58] Field of Search ....... 128/869, 870, 857, DIG. 23; 602/17, 18; 5/630, 636, 637

[56] References Cited

U.S. PATENT DOCUMENTS

| | | | |
|---|---|---|---|
| 3,783,863 | 1/1974 | Kliever | 128/870 |
| 3,897,777 | 8/1975 | Morrison | 128/133 |
| 4,058,112 | 11/1977 | Johnson | 5/637 |
| 4,182,322 | 1/1980 | Miller | 128/133 |
| 4,297,994 | 11/1981 | Bashaw | 128/133 |
| 4,528,981 | 7/1985 | Behar | 128/870 |
| 4,589,407 | 5/1986 | Koledin et al. | 128/87 |
| 4,612,678 | 9/1986 | Fitsch | 128/870 |
| 4,640,275 | 3/1987 | Buzzese et al. | 128/133 |
| 4,655,206 | 4/1987 | Moody | 128/870 |
| 4,854,305 | 8/1989 | Bremer | 128/75 |
| 4,905,712 | 3/1990 | Bowlin et al. | 128/870 |
| 5,265,625 | 11/1993 | Bodman | 128/870 |

*Primary Examiner*—Michael A. Brown

[57] ABSTRACT

A head immobilizer comprising a pair of complementary blocks sized and shaped to snugly fit about opposing sides of a patient's head during transportation, each block including a curved portion for disposition alongside the patient's head, a neck portion for disposition adjacent the patient's neck, and an upper tapered portion to permit the neck portions to be inwardly movable with respect to each other when the head portions are adjacent the patient's head whereby to permit the neck portions to be urged snugly against the patient's neck regardless of the size of the patient's head.

4 Claims, 1 Drawing Sheet

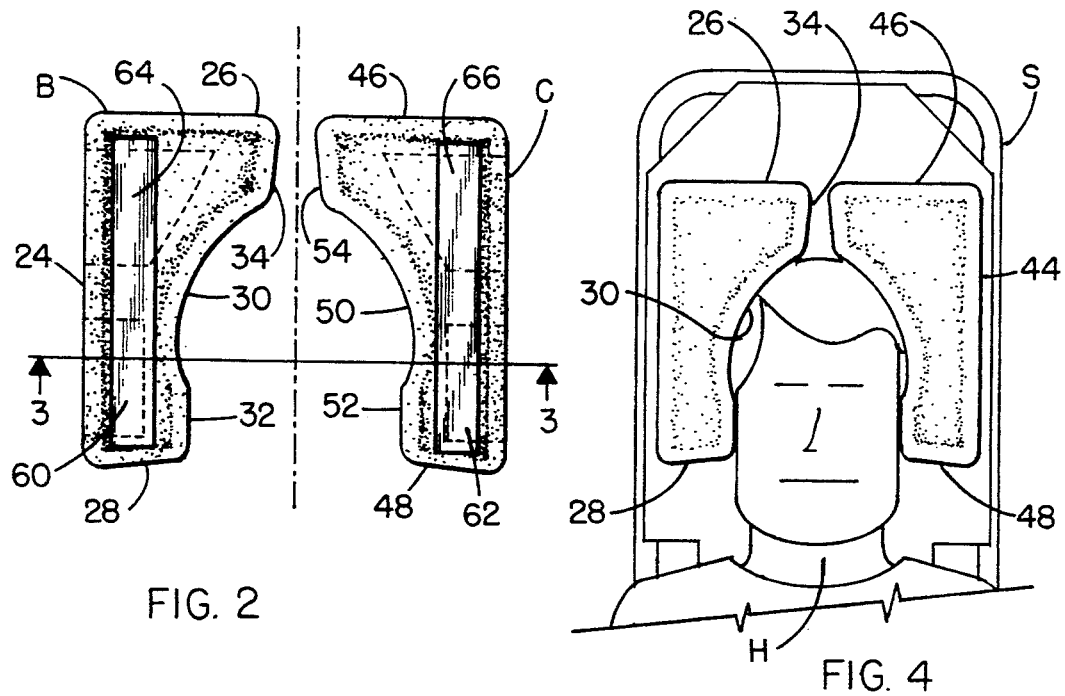
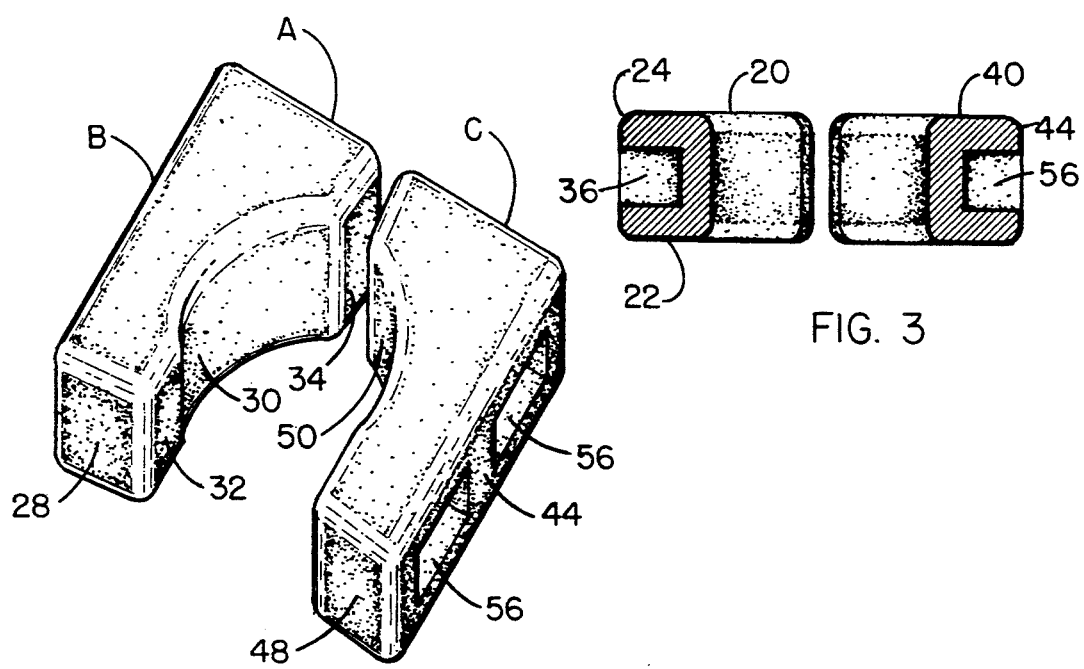

EMERGENCY HEAD IMMOBILIZERS

This invention relates to head Immobilizers for use in transporting patients from accident scenes to trauma care facilities.

In transporting patients where spinal injuries are not ruled out, medical emergency personnel are required to immobilize the patient's head and body during transportation. For many years, sandbags taped to the stretcher on opposing sides of the patient's head achieved this purpose. More recently rigid collars and cloth straps have been used. To reduce exposure to AIDS and HIV, OSHA has now established a "Bloodborne Pathogens" regulation which requires that emergency transportation equipment must either be sterilized after each use or discarded. Sterilizing strap restraints is an expensive, time consuming, and usually futile process. Logistics problems exist. There is an immediate need for a head immobilizer which is adapted for use on metal stretchers, adjustable to fit all sizes of heads from infant to adult, simple to use, light in weight, inexpensive and which assures compliance with OSHA's Blood Pathogen regulations prohibiting reusability.

DESCRIPTION OF THE INVENTION IN THE DRAWINGS:

FIG. 1 depicts an isometric view of a preferred embodiment of our invention;

FIG. 2 depicts a bottom view thereof;

FIG. 3 depicts a sectional view taken along lines 3—3 of FIG. 2; and

FIG. 4 is a view showing the invention in use mounted on a stretcher.

The specification will be easier to follow when it is understood that directional words are used with reference to the medical emergency personnel and the body of the patient. Hence "face" will refer to that portion of the described object which is presented in the same direction as the patient's face; "back", like the patient's back would be touching the face of the stretcher; "upper" will refer to the part of the object which is furthest from the patient's feet as he lies on the stretcher, and "lower" will refer to the part of the object which is closest to the patient's feet as he lies on the stretcher; "lateral" will refer to the part of the object which is to the patient's side as he lies on the stretcher, and "inner" will refer to the part of the object which is closest to the patient's midline as he lies on the stretcher.

Referring now in more detail, and by reference character to the drawings which illustrate a preferred embodiment of my invention, A designates a head immobilizing device comprising a pair of complimentary support blocks, B, C, preferably though not necessarily made of styrofoam. Each block has substantial thickness and includes faces 20, 40, respectively, and backs 22, 42, respectively. The block B includes side 24, top 26 and foot 28. The block B also includes an elongated curved portion 30, and a neck area 32 which is flat and disposed between the curved portion 30 and the foot 28. The block B is wider at the curved portion 30 than at the foot 28, and at the top 26 is provided with an outwardly extending margin 34 which extends away from the top 30 and merges with the curved portion 30. The side 24 is provided with spaced gripping recesses 36 for purposes presently more fully to appear.

Similarly the block C includes a side 44, top 46 and foot 48. The block C also includes a curved portion 50, a flat neck area 52 and a laterally outwardly extending margin 54 which is tapered and disposed between the top 46 and the curved portion 50. The side 44 is similarly provided with spaced gripping recesses 56.

Adhesively attached to the backs 22, 42, respectively are elongated, double-faced adhesive strips 60, 62, one side of which is secured to the blocks B and C respectively, and the other side of which contains outwardly presented peel-away covers 64, 66.

USE

In use, referring to FIG. 3, after the patient has been placed on the stretcher S with his/her head H near one end thereof, the patient's head H is placed in the desired position, the peel-away cover 64 is removed from the block B, the block B is positioned snugly against the right side of the head H, and when in position the block B is pressed firmly against the metal stretcher S, whereby the adhesive strip 60 secures the block B in position against the stretcher S. Thereafter, the peel-away cover 66 is removed from the block C, the block C is positioned snugly against the left side of the head H, and when in position the block C is pressed firmly against the metal stretcher S, whereby the adhesive strip 62 secures the block C in position against the stretcher S. Tape (not shown) is applied from one side of the stretcher S to the other, across the blocks B and C, and the patient's head H, whereby the patient's head H and neck are held fixed on the stretcher S during transportation.

After the patient has arrived at the care facility, and been taken off the stretcher, the blocks B and C are removed from the stretcher by placing one's hands in the recesses 36, 56, and pulling the blocks B, C, respectively away from the stretcher S. However, because of the properties of the foam material used in the construction of the blocks B and C, the strips 60, 62, and part of the blocks B and C remain attached to the stretcher S and the blocks B and C are pulled apart and made incapable of being reused. The portions of blocks B and C which have adhered to the stretcher S are readily removable during post usage sterilization procedures.

Because styrofoam is relatively inexpensive and an easily molded material, it is an economic advantage to be able to discard blocks at lees cost than what would be required to clean and sterilize the presently used blocks and straps. Additionally, the tapered upper margins 34, 54, made the blocks B, C adaptable to patients of all ages, because such tapers permit the necks 32, 52 to move closer together for stabilizing the head and necks of child patients.

It should be apparent that changes and substitutions in the unique and novel arrangement, combination, assembly and interaction of the various parts and components shown and described herein may be made without departing from the nature and principle of my invention.

Having thus described my invention, what I claim and desire to secure by Letters Patent is shown in the drawings, described in the specification and claimed in the following claims:

1. A head immobilizing device for use on a stretcher comprising a pair of complementary blocks of material, each block having a top, foot, face, back, outer lateral surface and inner lateral surface, said inner lateral surface including a round section, a flat section and a tapered section, said round section being contoured for snug fitting disposition about the head of a patient lying on a stretcher, said flat section being sized for snug fitting disposition along the side of said patient's neck when the round section is disposed against the side of the patient's head, and said tapered section being such that the blocks are closer together at their tops than at their round sections, whereby the tops of the blocks can be pivoted with respect to each other and thereby immobilize the top of the patient's head as well as the neck and sides thereof as the patient is transported on the stretcher.

2. The device of claim 1 in which each block is provided on its back with adhesive means for securing the block to the stretcher and is fabricated of a material which will break apart when upward force is applied in attempts to pull the block free from the stretcher.

3. The device of claim 2 in which the blocks are fabricated of styrofoam.

4. The device of claim 1 in which each block is provided on its back with adhesive means for securing the block to the stretcher by pressing the same downwardly on the stretcher after it has been positioned with respect to the patient's head and is fabricated of a material which will break apart when upward force is applied in attempts to pull the block free from the stretcher.

* * * * *